United States Patent [19]
Stevenson et al.

[11] Patent Number: 5,959,829
[45] Date of Patent: Sep. 28, 1999

[54] CHIP CAPACITOR ELECTROMAGNETIC INTERFERENCE FILTER

[75] Inventors: Robert A. Stevenson, Canyon Country, Calif.; Donald K. Haskell, Minden, Nev.; Richard L. Brendel, Carson City, Nev.; Jason Woods, Carson City, Nev.; Mike Louder, Carson City, Nev.

[73] Assignee: Maxwell Energy Products, Inc., San Diego, Calif.

[21] Appl. No.: 09/027,115

[22] Filed: Feb. 18, 1998

[51] Int. Cl.⁶ .................................................. H01G 4/35
[52] U.S. Cl. ...................... 361/302; 361/303; 361/306.1; 361/309; 333/182
[58] Field of Search ............................... 361/301.2, 301.3, 361/302, 303, 306.2, 306.3, 307–308.1, 308.3, 311–313, 321.2, 329; 174/50.5, 50.51, 50.52, 50.54, 262, 152 GM, 158 R, 143, 151, 52.1; 333/182–185; 29/25.42; 607/36, 37, 5

[56] References Cited

U.S. PATENT DOCUMENTS

| | | |
|---|---|---|
| 2,756,375 | 7/1956 | Peck . |
| 3,235,939 | 2/1966 | Rodriguez et al. . |
| 3,617,830 | 11/1971 | Perna, Jr. ................................ 361/329 |
| 3,920,888 | 11/1975 | Barr . |
| 4,083,022 | 4/1978 | Nijman . |
| 4,148,003 | 4/1979 | Colburn et al. . |
| 4,152,540 | 5/1979 | Duncan et al. . |
| 4,220,813 | 9/1980 | Kyle . |
| 4,247,881 | 1/1981 | Coleman . |
| 4,314,213 | 2/1982 | Wakino . |
| 4,352,951 | 10/1982 | Kyle . |
| 4,362,792 | 12/1982 | Bowsky et al. . |
| 4,421,947 | 12/1983 | Kyle . |
| 4,424,551 | 1/1984 | Stevenson . |
| 4,456,786 | 6/1984 | Kyle . |
| 4,500,159 | 2/1985 | Briones et al. . |
| 4,737,601 | 4/1988 | Gartzke . |
| 4,741,710 | 5/1988 | Hogan et al. . |
| 5,032,692 | 7/1991 | DeVolder . |
| 5,070,605 | 12/1991 | Daglow et al. . |
| 5,333,095 | 7/1994 | Stevenson et al. . |
| 5,406,444 | 4/1995 | Selfried et al. ........................ 361/302 |
| 5,531,003 | 7/1996 | Seifried et al. ....................... 29/25.42 |
| 5,620,476 | 4/1997 | Truex et al. . |
| 5,650,759 | 7/1997 | Hittman et al. . |
| 5,735,884 | 4/1998 | Thompson et al. ..................... 607/36 |
| 5,759,197 | 6/1998 | Sawchuk et al. ........................ 607/36 |

OTHER PUBLICATIONS

Article entitled "Carts '97"; published Mar. 24, 1997; sponsored by The Components Technology Institute, Inc.; 11 pages.

*Primary Examiner*—Dean A. Reichard
*Assistant Examiner*—Anthony Dinkins
*Attorney, Agent, or Firm*—Kelly Bauersfeld Lowry & Kelley, LLP

[57] ABSTRACT

An electromagnetic interference (EMI) filter capacitor assembly is provided for shielding and decoupling a conductive terminal pin or lead of the type used, for example, in an implantable medical device against passage of external interference signals. The EMI filter is constructed of relatively inexpensive ceramic chip capacitors which replace relatively expensive feedthrough capacitors as found in the prior art. The chip capacitors are mounted directly onto a hermetic feedthrough terminal in groups of two or more which vary in physical size, dielectric material and capacitance value so that they self-resonate at different frequencies. This "staggering" of resonant frequencies and direct installation at the hermetic terminal provides the EMI filter with sufficient broadband frequency attenuation. In one preferred form, multiple chip capacitor groupings are mounted onto a common base structure, with each capacitor grouping associated with a respective terminal pin. In another preferred form, a non-conductive substrate is provided with metalized circuit traces to better accommodate the mounting of the chip capacitors. Additionally, novel chip capacitor geometry/termination-metallization is provided which significantly reduces the internal inductance of the capacitor to improve its high frequency performance as an EMI filter.

20 Claims, 8 Drawing Sheets

| | |
|---|---|
| SRF₁ | 1000 pf CHIP CAPACITOR |
| SRF₂ | 500 pf CHIP CAPACITOR |
| SRF₃ | 50-100 pf CHIP CAPACITOR |

CHIP CAPACITOR ELECTROMAGNETIC INTERFERENCE FILTER

BACKGROUND OF THE INVENTION

This invention relates generally to EMI filter terminal pin subassemblies and related methods of construction, particularly of the type used in implantable medical devices such as cardiac pacemakers and the like, to decouple and shield undesirable electromagnetic interference (EMI) signals from the device. More specifically, the present invention relates to a ceramic chip capacitor EMI filter assembly and related installation method, including utilization of groupings of a plurality of chip filter capacitors which vary in capacitance value.

Implantable medical devices employ a wide variety of leads which are placed in body tissue or fluids. These include but are not limited to atrial/ventricle unipolar, atrial/ventricle bipolar, subcutaneous patch, transthoracic impedance monitor, telemetry, cochlear implants and the like. In some implantable defibrillator designs the metallic case or housing of the device acts as one electrode or lead. Leads which are closely spaced together in the body (such as bipolar) tend to pick up EMI signals which are in phase (common mode EMI). Lead schemes which have substantial separation between the leads and are close to an emitter (such as a cellular phone) tend to pick up EMI signals which are not in phase (differential mode EMI). In addition, certain implantable medical device sensing circuits are highly sensitive (such as unipolar atrial blood pool sensing leads) which tends to make them more susceptible to EMI. Other implantable device circuits may be limited in the amount of capacitance to ground that they can tolerate (certain defibrillator high voltage outputs or transthoracic impedance monitors, for example).

Feedthrough terminal pin assemblies are generally well known in the art for connecting electrical signals through the housing or case of an electronic instrument. For example, in implantable medical devices such as cardiac pacemakers, defibrillators or the like, the hermetic terminal pin assembly comprises one or more conductive terminal pins supported by an insulator structure for feedthrough passage from the exterior to the interior of the medical device. Many different insulator structures and related mounting methods are known in the art for use in medical devices wherein the insulator structure also provides a hermetic seal to prevent entry of body fluids into the housing of the medical device. However, the feedthrough terminal pins are typically connected to one or more lead wires which effectively act as an antenna and thus tend to collect stray EMI signals for transmission into the interior of the medical device.

There are two primary ceramic capacitor geometries in common use in the industry—the rectangular chip and the feedthrough (often called a discoidal capacitor). The ceramic monolithic rectangular chip capacitor (or "chip capacitor") is produced in very high commercial volumes in highly automated facilities. Over the years the cost of ceramic chip capacitors has dropped a great deal. It is now common to purchase certain value chip capacitors for only a few pennies. The ceramic feedthrough capacitor is only produced in a small fraction of the chip capacitor volume. Accordingly, feedthrough capacitor production has not been nearly as automated. In addition, the feedthrough capacitor is inherently more expensive to produce due to drilling and centering the through hole, tighter dimensional control, reduced volumetric efficiency and difficulty in automating the manufacturing process. Typically the cost of a particular value chip capacitor is ten to twenty percent of the cost of an equivalent value discoidal feedthrough capacitor. Because of the trend in the medical device industry to reduce cost, it would be highly desirable to use relatively inexpensive ceramic chip capacitors in place of feedthrough capacitors, where practicable.

Previously, the feedthrough capacitor-type has been the capacitor of choice for use in high performance or broadband EMI filters because it provides effective attenuation over very wide frequency ranges. A serious shortcoming of the rectangular chip capacitor is that its equivalent circuit model consists of a capacitor in series with a lumped inductor (the inductance comes from its leads, internal electrode plates and connection wiring). This means that all chip capacitors will self resonate when their inductive reactance and capacitive reactance become equal. The frequency in MHz at which this occurs is defined as the "self resonant frequency" or SRF, which is determined in accordance with the formula:

$$SRF = \frac{1}{2\pi\sqrt{LC}}$$

wherein, L=Inductance in microhenries, and
C=Capacitance in microfarads.

Above the SRF, the chip capacitor becomes increasingly inductive and ceases to be an effective EMI filter. The unique geometry of the feedthrough capacitor, however, eliminates this lumped series inductance. Accordingly, a properly designed and installed feedthrough capacitor does not have a SRF above which it becomes an inductor (feedthrough capacitors do exhibit a minor self resonance, but continue to perform as an effective capacitor bypass element above this SRF).

Two different general approaches are commonly used to eliminate or reduce stray or unwanted EMI signals. One very effective but relatively costly approach is where the hermetic terminal pin assembly has been combined directly with a ceramic feedthrough filter capacitor to decouple interference signals to the housing of the medical device. In a typical unipolar construction as shown in U.S. Pat. No. 5,333,095, a coaxial ceramic feedthrough filter capacitor is used in a feedthrough assembly to suppress and decouple undesired interference or noise transmission along a terminal pin. The feedthrough filter capacitor comprises a so-called discoidal capacitor having two sets of electrode plates embedded in spaced relation within an insulative dielectric substrate or base, formed typically as a ceramic monolithic structure. One set of the electrode plates is electrically connected at an inner diameter cylindrical surface of the discoidal capacitor structure to the conductive terminal pin utilized to pass the desired electrical signal or signals. The other or second set of electrode plates is coupled at an outer diameter surface of the discoidal capacitor to a cylindrical ferrule of conductive material, wherein the ferrule is electrically connected in turn to the conductive housing of the electronic device. The number and dielectric thickness spacing of the electrode plate sets varies in accordance with the capacitance value and the voltage rating of the discoidal capacitor. The outer feedthrough capacitor electrode plate sets (or "ground" plates) are coupled in parallel together by a metalized band which is, in turn, coupled to the ferrule by conductive adhesive, soldering, brazing, or the like. The inner feedthrough capacitor electrode plate sets (or "active" plates) are coupled in parallel together by a metalized band which is, in turn, coupled to the lead wire(s) by conductive adhesive, soldering, brazing, or the like. In operation, the feedthrough capacitor permits passage of relatively low frequency electrical signals along the terminal pin while shielding and decoupling/attenuating undesired interference signals of typically high frequency to the conductive housing. Feedthrough capacitors of this general type are available in unipolar (one), bipolar (two), tripolar (three), quadpolar (four), pentapolar (five), hexpolar (6) and additional lead configurations. The feedthrough capacitors of this general type are commonly employed in implantable cardiac pacemakers and defibrillators and the like, wherein the pacemaker housing is constructed from a biocompatible metal, such as titanium alloy which is electrically coupled to the feedthrough filter capacitor. As a result, the filter capacitor and terminal pin assembly prevents entrance of interference signals to the interior of the pacemaker housing, wherein such interference signals could otherwise adversely affect the desired cardiac pacing or defibrillation function. Also see for example, the feedthrough capacitor subassemblies disclosed in U.S. Pat. Nos. 3,920,888; 4,152,540; 4,421,947; 4,424,551 and 5,333,095.

A second type of EMI filter approach in common use in implantable medical devices involves installation of ceramic chip capacitors on the circuit board, substrate or flex cables leading to the hermetic feedthrough terminal. For example, it is known to locate an EMI low pass filter and related chip capacitors on the circuit board or substrate of an implantable medical device, or to mount a chip capacitor onto a circuit flex cable near the hermetic terminal of a pacemaker. These are very cost effective methods, but they do not make a very effective EMI filter, particularly over broad frequency ranges. Both of these approaches provide ineffective EMI filters at high frequencies due to the parasitic resonance and coupling caused by the substantial inductance and capacitance of the circuit traces and connecting wires. The physical separation of the chip capacitors from the point of penetration into the shield housing (the hermetic seal terminal) creates excessive loop inductance and allows the unwanted signals to penetrate to the interior of the shield. Once the EMI is inside, it is very difficult to control as it will tend to couple across filtering elements to sensitive circuitry.

Accordingly, there is a need for an EMI filter that utilizes cost effective ceramic chip capacitors in a manner to achieve the beneficial EMI filtering characteristics similar to feedthrough filter capacitors. Such a unique EMI filter should utilize chip capacitors that are mounted in groups which vary in physical size, dielectric material and capacitance value so that they self-resonate at different frequencies to provide the filter desirable broadband frequency attenuation. Morever, a novel method of chip capacitor geometry/termination-metallization is needed which significantly reduces the internal inductance of the chip capacitor to improve its high frequency performance as an EMI filter. The present invention fulfills these needs and provides other related advantages.

SUMMARY OF THE INVENTION

The present invention resides in an electromagnetic interference (EMI) filter assembly for shielding and decoupling of a conductive terminal pin or lead of the type used, for example, in an implantable medical device such as a cardiac pacemaker or cardioverter defibrillator against passage of external interference signals, such as caused by digital cellular phones. The EMI filter assembly as described herein is constructed of relatively inexpensive ceramic chip capacitors which replace the relatively expensive feedthrough filter capacitors in prior art EMI filter assemblies. The EMI filter assembly of the present invention is disposed at the point of lead penetration through a conductive substrate and comprises, generally, at least one conductive terminal which is associated with the point of lead penetration through the conductive substrate, and means for mounting the at least one conductive terminal within an opening formed in the conductive substrate, with the conductive terminal and the substrate in non-conductive relation. A plurality of chip capacitors of differing capacitance values are provided which each have first and second sets of electrode plates. The first set of electrode plates is conductively coupled to the at least one conductive terminal, and the second set of electrode plates is conductively coupled to the conductive substrate. By installing the chip capacitors as close as possible to the point of lead penetration through the conductive substrate, external series inductance due to lead wires is reduced. This also reduces the chance of electromagnetic interference re-radiating or coupling around the EMI filter assembly.

More particularly, the at least one conductive terminal may comprise a plurality of conductive terminals which are associated with the point of lead penetration through the conductive substrate. The chip capacitor groupings may be designed asymmetrically to limit the capacitance to ground on certain sensitive electronic circuits or be installed to provide additional differential mode attenuation when required. Further, a terminal-to-terminal chip capacitor may be provided that has a first set of electrode plates coupled to one conductive terminal, and a second set of electrode plates coupled to another conductive terminal.

The conductive substrate may comprise a ferrule that is conductively attachable to a housing for an electronic device. Alternatively, the conductive substrate may comprise metallization applied to an insulative substrate wherein the applied metallization further forms the at least one conductive terminal. In this particular embodiment, the conductive terminal and the conductive substrate have matched coefficients of expansion.

The chip capacitors may comprise a reduced inductance design wherein the first set of electrode plates terminates on one side of the chip capacitor perpendicular to the first set of electrode plates, and the second set of electrode plates terminates on the remaining sides of the chip capacitor perpendicular to the second set of electrode plates. Another embodiment of the invention may include a semicircular recess for receiving a conductive terminal pin therein. In yet another embodiment, the chip capacitor may comprise a wedge-shaped chip capacitor having the second set of electrode plates terminating on three sides thereof.

The present invention provides a means by which the chip capacitors may be installed directly at the point of lead penetration through a conductive substrate, and utilizes multiple chip capacitors to stager their self-resonant points in such as way as to provide adequate electromagnetic interference (EMI) filter attenuation over a broad frequency range, including the hand-held wireless personal communication device (cellular telephone) band from 935 MHZ to 1.8 GHz. Further, the novel chip capacitor designs illustrated herein reduce the inductance of the capacitors and/or facilitate packing at the point of lead penetration through the conductive substrate.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIGS. 12A–12D illustrate a novel method of reducing the series inductance of a chip capacitor by terminating the ground plates on three sides instead of just the end, wherein:

FIGS. 13A–13D illustrates an improved method relative to the chip capacitor of FIGS. 12A–12D for reducing the series inductance of a chip capacitor, where the form factor is adjusted to minimize the loop inductance, wherein:

FIGS. 14A–14D are similar to FIGS. 12 and 13, with the exception that a semicircular recess is provided in one side of the chip capacitor to facilitate mounting directly to a lead at the point of penetration into a device housing, wherein:

FIGS. 16A–16D illustrate yet another unique geometry wherein the chip capacitor is wedge-shaped to provide higher volumetric efficiency and shielding when butted around a lead wire, wherein:

DETAILED DESCRIPTION OF THE PREFERRED EMBODIMENTS

Figures 1, 2, 3, 4:
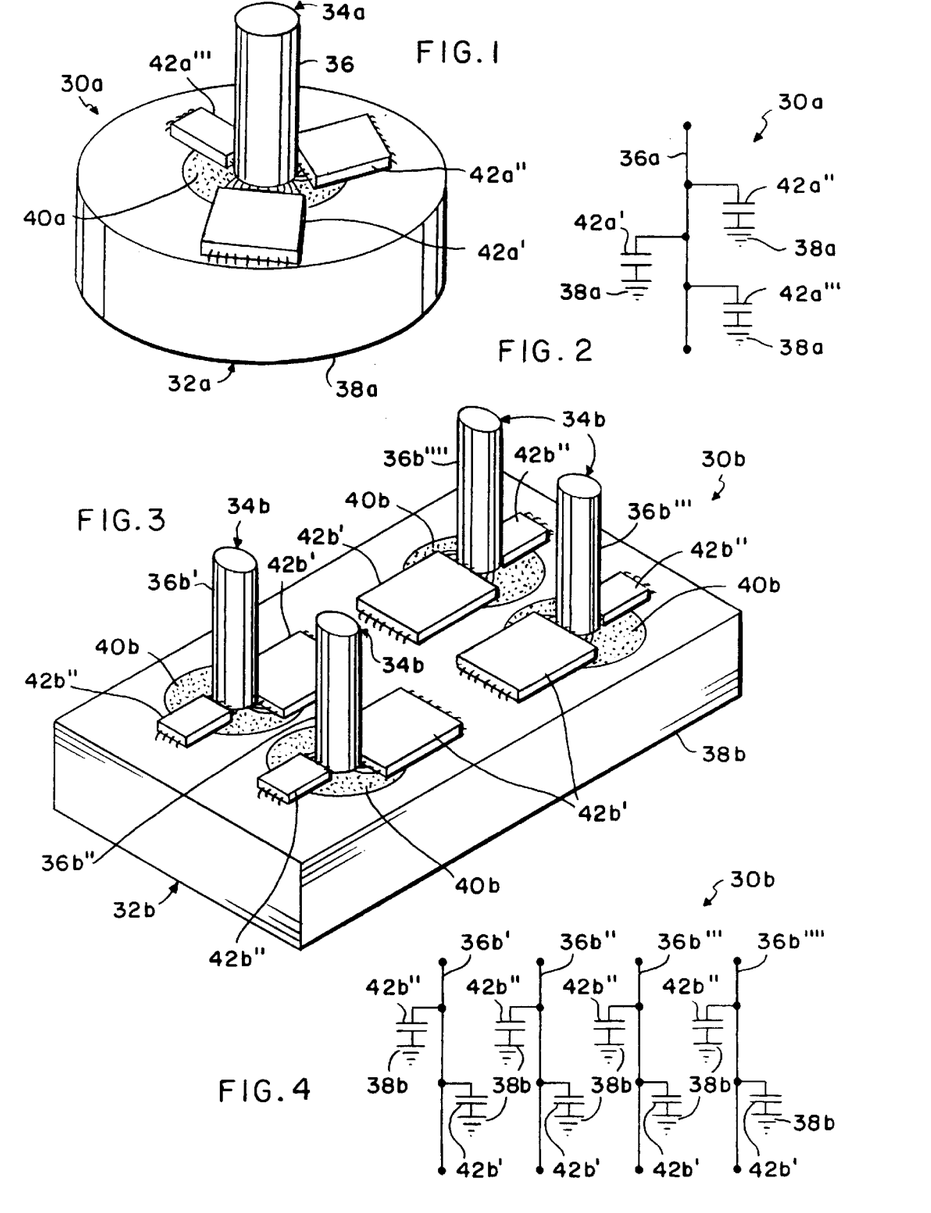
FIG. 1 is a perspective view of a unipolar pacemaker hermetic terminal incorporating the novel chip capacitor EMI filter of the present invention, wherein the filter is located at a terminal header of the implantable medical device and comprises a grouping of three chip capacitors.
FIG. 2 is an electrical schematic of the assembly shown in FIG. 1.
FIG. 3 is a perspective view of a quadpolar hermetic terminal for an implantable defibrillator, wherein the chip capacitor EMI filter comprises groupings of two chip capacitors.
FIG. 4 is an electrical schematic of the assembly shown in FIG. 3.
Figures 5, 6:
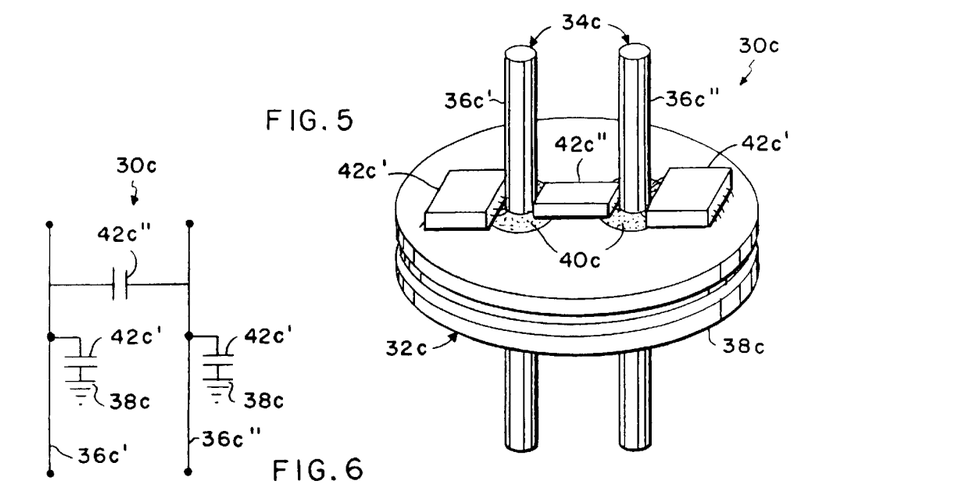
FIG. 5 is perspective view of a round cardiac pacemaker terminal incorporating the present invention, wherein single chip capacitors are connected from the lead to the housing, and an additional chip capacitor is connected from lead-to-lead to provide additional differential mode filtering.
FIG. 6 is an electrical schematic of the assembly shown in FIG. 5.
Figures 7, 8:
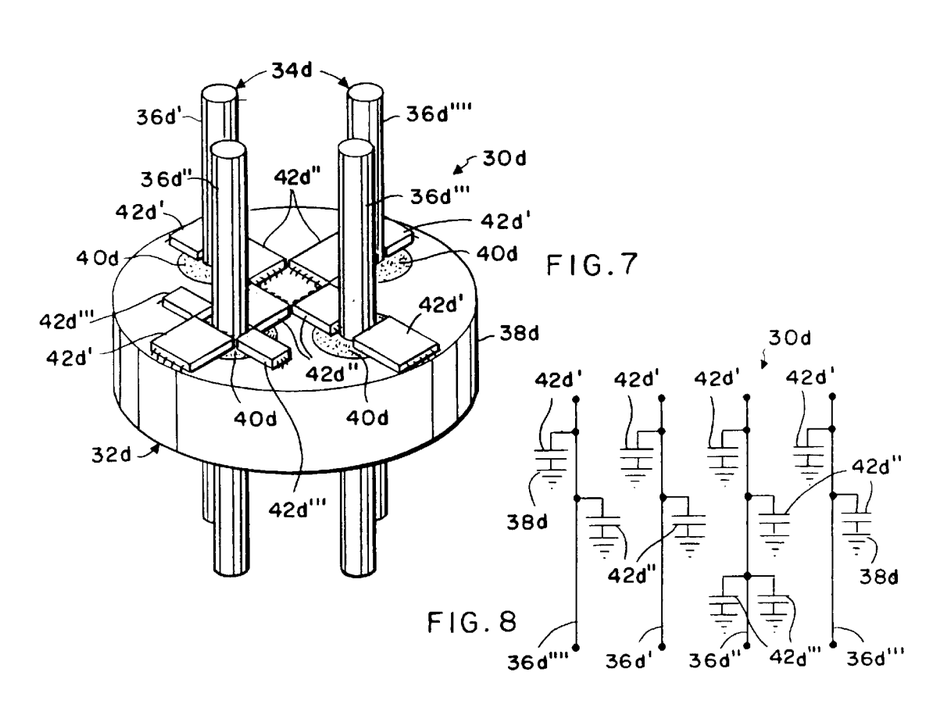
FIG. 7 is a perspective view of a round asymmetrical quadpolar terminal incorporating the EMI filter of the present invention, wherein the terminal includes groupings of two chip capacitors on three of its terminals, and a grouping of four chip capacitors on a fourth terminal to provide additional attenuation for a particularly sensitive circuit.
FIG. 8 is an electrical schematic of the assembly shown in FIG. 7.
Figure 9:
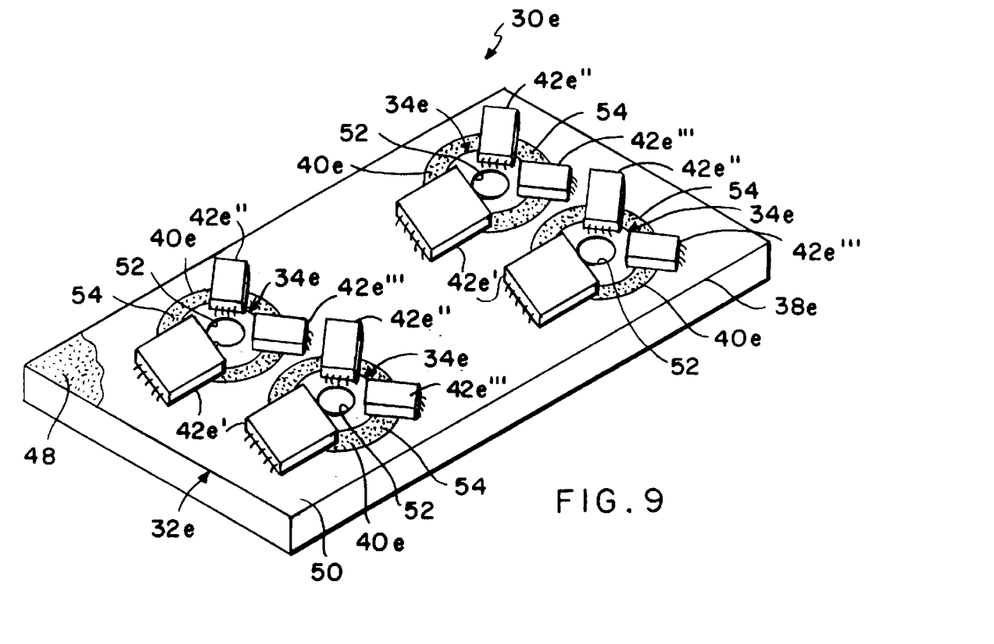
FIG. 9 illustrates a method of mounting the chip capacitors to an alumina substrate which also forms a hermetic seal.
Figure 15:
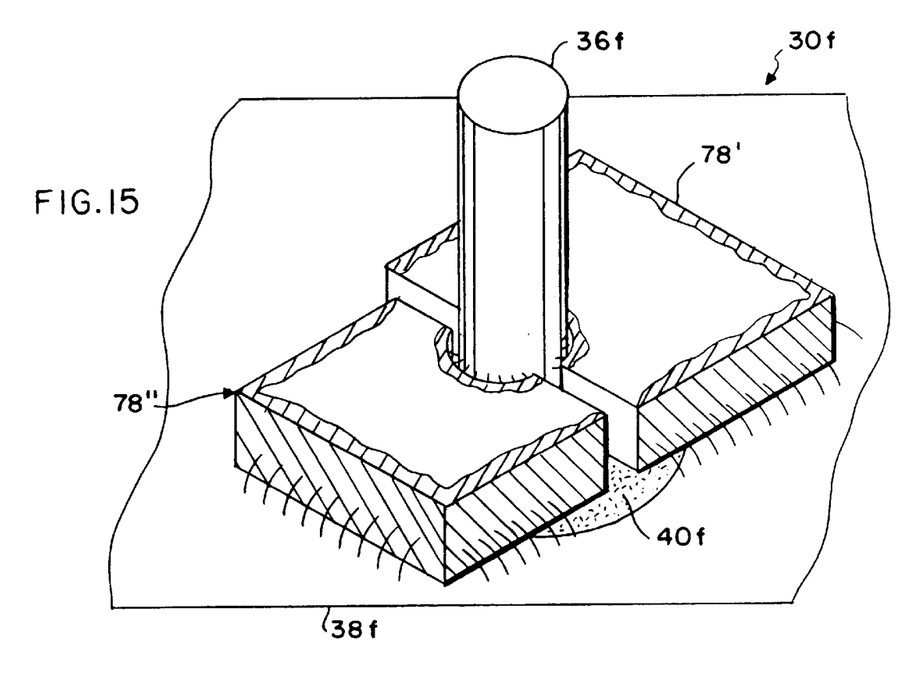
FIG. 15 is a perspective view of an EMI filter embodying the present invention utilizing two differently sized chip capacitors similar to that illustrated in FIGS. 14A–14D.
Figure 17:
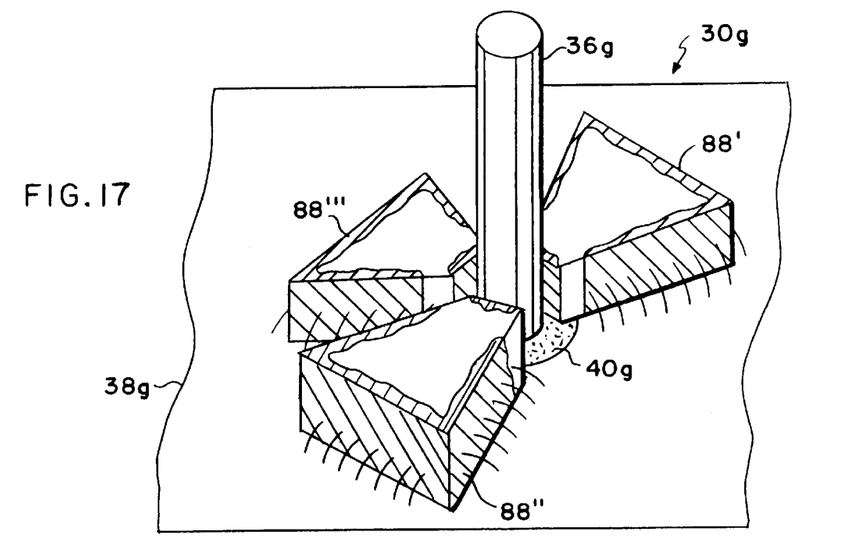
FIG. 17 is a perspective view illustrating the manner in which three wedge-shaped chip capacitors similar to those illustrated in FIGS. 16A–16D, are conductively attached to a terminal lead and mounted in spaced relation thereabout on a grounded housing to provide desired EMI filtering characteristics in accordance with the present invention.

As shown in the drawings for purposes of illustration, the present invention is concerned with a novel electromagnetic interference (EMI) filter assembly generally designated in FIGS. 1 and 2 by the reference number 30a, in FIGS. 3 and 4 by the reference number 30b, in FIGS. 5 and 6 by the reference number 30c, in FIGS. 7 and 8 by the reference number 30d, in FIG. 9 by the reference number 30e, in FIG. 15 by the reference number 30f, and in FIG. 17 by the reference number 30g. In the following description, functionally equivalent elements of the various embodiments will share the same reference number differentiated by the lower case letter applied to the various embodiments as set forth above. The improved EMI filter assemblies 30a–30g are, importantly, disposed at the point of lead penetration through a conductive substrate 32 and comprise, generally, one or more conductive terminals 34 that are typically comprised of terminal pins 36, and a conductive ferrule 38 through which the terminal pin(s) passes in non-conductive relation. An insulator 40 supports each conductive terminal pin 36 from the conductive ferrule 38 in electrically insulated relation.

In accordance with the present invention, a plurality of chip capacitors 42 are provided in association with each terminal pin 36 at the point of lead penetration through the ferrule 38. Each chip capacitor 42 is of standard construction to include first and second sets of electrode plates 44 and 46. The first set of electrode plates 44 is conductively coupled to the respective conductive terminal 34, 36, and the second set of electrode plates is conductively coupled to the conductive substrate 32, 38. Typically, the conductive ferrule 38 is conductively mounted to, for example, a housing for an implantable medical device, and the ferrule and housing cooperatively form the conductive substrate 32.

While the invention is primarily designed for use in cardiac pacemakers (bradycardia devices), cardioverter defibrillators (tachycardia devices), internal drug pumps, cochlear implants and other medical implant applications, it is also applicable to a wide range of EMI filter applications such as military or space electronic modules where it is desirable to preclude the entry of electromagnetic interference (EMI) into a hermetically sealed housing containing sensitive electronic circuitry.

Referring now to the drawings, FIGS. 1–9 illustrate various chip capacitor EMI filters 30a–30e incorporating the present invention and located at the terminal header of an implantable medical device. More particularly, FIGS. 1–9 illustrate various groupings of chip capacitors 42 in accordance with the invention. In this regard, the present invention eliminates the need for the relatively expensive feedthrough capacitor assemblies which are commonly utilized in the prior art. The chip capacitors 42 are uniquely installed by mounting directly onto a hermetic feedthrough terminal in groups which vary in physical size, dielectric material and capacitance value. The capacitors 42 are typically mechanically and electrically attached on one end to a titanium ferrule/header 38 (or other metal ground surface) by welding, brazing, soldering, conductive thermoset adhesive, mechanical spring fingers or the like. The other end of the chip capacitor 42 is typically attached mechanically and electrically to the platinum (or other metal) lead wire or terminal pin 36 of the medical device terminal header by welding, brazing, soldering, conductive thermoset adhesive, mechanical spring fingers or the like. The groupings of chip capacitors are selected such that they self-resonate at different frequencies. This "staggering" of resonant frequencies and direct installation at the hermetic terminal provides the EMI filter with broadband frequency attenuation. An important aspect of the invention is the location of the chip capacitors 42 directly at the point of lead penetration at the header of the implantable device. The efficacy of the chip capacitor filter as described herein is based upon attenuation of the RF carrier of the electromagnetic interference (EMI) before it can enter into the sealed housing for the electronic circuitry, and potentially re-radiate or couple to sensitive internal circuits.

FIGS. 1 and 2 illustrate a unipolar EMI filter assembly 30a wherein a terminal pin 36a extends through a conductive ferrule 38a in nonelectrically conducting relation. This is accomplished by means of the insulator 40a. Three chip capacitors 42a'–42a''' are spaced about the terminal pin 38a such that each respective first set of electrode plates is conductively coupled to the terminal pin 36a, and each respective second set of electrode plates is conductively coupled to the conductive ferrule 38a. The chip capacitors 42a'–42a''' are located at the terminal header (i.e., the point of entry of the terminal pin 36a through the ferrule 38a) of the associated electronic device.

FIGS. 3 and 4 illustrate an alternative embodiment, namely a rectangular quadpolar hermetic terminal for an implantable defibrillator with groupings of two chip capacitors 42b' and 42b'' associated with each one of the four terminal pins 36b'–36b'''' extending through the conductive ferrule 38b. As is typically the case, the terminal pins 36b'–36b'''' are supported within the ferrule 38b in nonconductive relation by means of respective insulators 40b.

FIGS. 5 and 6 illustrate another alternative EMI filter assembly 30c embodying the present invention, comprising a round cardiac pacemaker terminal with single chip capacitors 42c' connected from the respective terminal pins 36c' and 36c'' to the ferrule 38c (common mode EMI filter), and an additional chip capacitor 42c'' connected from terminal-to-terminal to provide additional differential mode filtering.

FIGS. 7 and 8 illustrate yet another EMI filter assembly 30d embodying the present invention, comprising a round asymmetrical quadpolar terminal with groupings of two chip capacitors 42d and 42d'' on three of its terminals 36d', 36d''', and 36d''''. A grouping of four chip capacitors 42d'–42d'''' is illustrated on the fourth terminal pin 36d'' to provide additional attenuation for a particularly sensitive circuit. For example, such an EMI filter assembly 30d might be useful in a floating unipolar sensing lead placed in the atrial blood stream.

FIG. 9 illustrates yet another EMI filter assembly 30e embodying the present invention. In particular, FIG. 9 illustrates a method of mounting the chip capacitors 42e'–42e''' to an insulative alumina substrate 48 which is capable of forming a hermetic seal with an associated conductive substrate. The top of the alumina substrate 48 is metalized 50 to provide a convenient ground attachment point for the chip capacitors 42e'–42e'''. The metallization 50 also provides effective RF shielding. The pattern of the metallization 50 may be varied to allow various sizes of chip capacitors 42e to be utilized. The pattern shown includes a conductive terminal pad 34e adjacent to apertures 52 through the substrate 48, separated from the remainder of the metallization layer 50 by a non-metalized separator band 54. The assembly shown is ready to mount to a plurality of terminal pins. An advantage of this particular construction of the EMI filter assembly 30e is that both the conductive terminals 34e and the conductive portion of the ferrule 38e have matched coefficients of expansion.

A novel feature of the present invention is that it can accommodate a wide range of chip capacitor EMI filter configurations in order to accommodate the lead/terminal and common/differential mode complexity. As shown in FIGS. 1–9, some of the designs of the filter assemblies 30a–30e are symmetrical which provide the same capacitance to ground and attenuation on each circuit. Other designs are asymmetrical which either limit the capacitance to ground on certain sensitive circuits or add line-to-line chip capacitors in order to provide additional differential mode attenuation.

Figure 10:
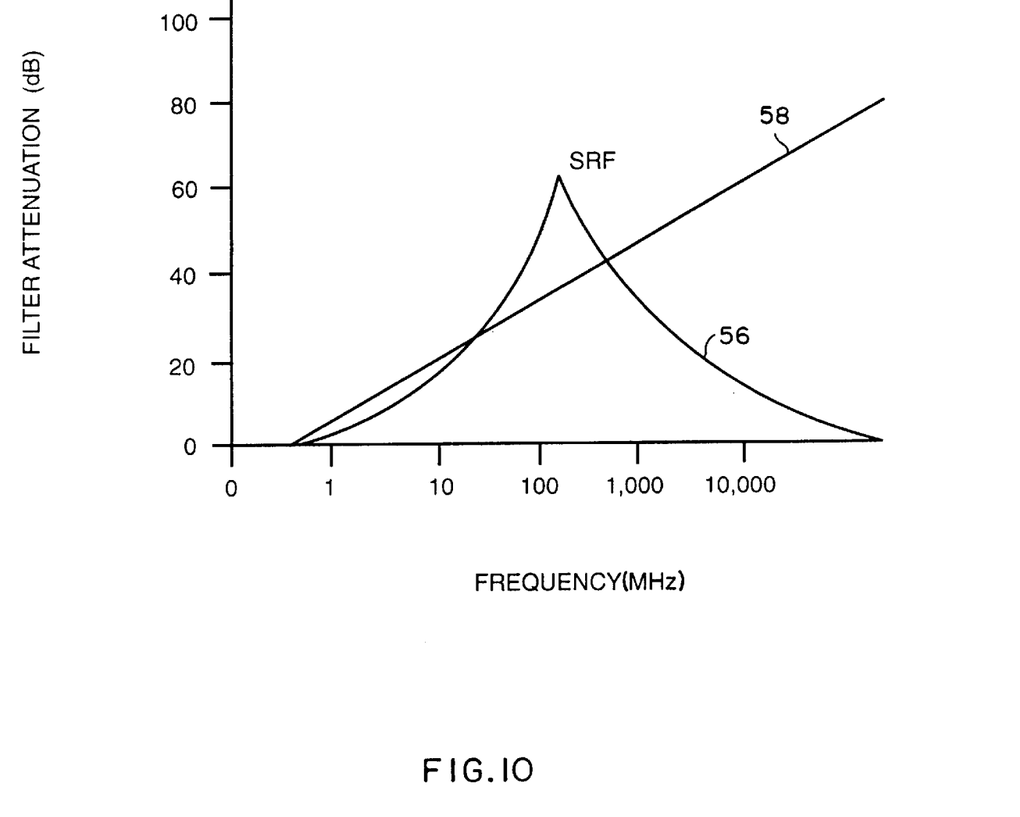
FIG. 10 is a diagram illustrating the attenuation characteristic of a 1,000 picofarad chip capacitor versus frequency.
Figure 11:
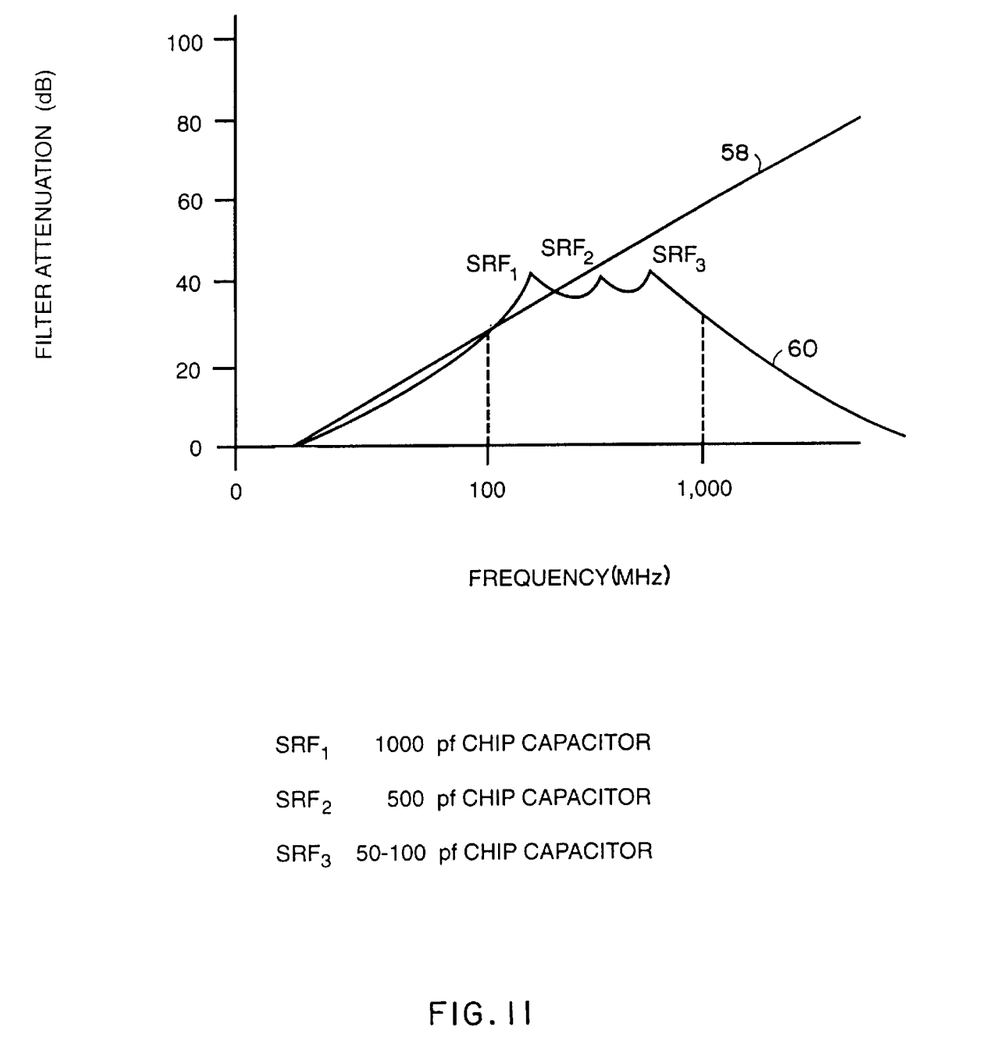
FIG. 11 is a diagram illustrating a composite curve of a grouping of three chip capacitors on a unipolar pacemaker circuit (FIG. 1), wherein the chip capacitors are of different capacitance values for the purpose of staggering of the resonant dips in high frequency attenuation in order to provide sufficient attenuation throughout a design frequency range.

Adding chip capacitors 42 of varying values and sizes provides staggering of resonant frequencies which makes the chip capacitor filter to be even more effective in the 950 MHZ to 1.8 GHz frequency range, in which hand-held personal communication devices (such as digital cellular telephones) are typically operated. In this regard, FIG. 10 shows the attenuation versus frequency characteristic of a single 1,000 picofarad chip capacitor 42. Its SRF is noted at 192 MHZ. Above 192 MHZ, the attenuation decreases as the capacitor becomes increasingly inductive (see curve 56). "Ideal" capacitor performance is indicated by the line 58. In comparison, FIG. 11 illustrates the effect of staggering a 1,000 pf, a 500 pf and a 100 pf chip capacitor in a grouping (for example as that shown in FIG. 1) located at the device header. The capacitors 42 may, of course, differ in shape, physical size, electrode plate count and dielectric material. They may also form an array as shown in the drawings. The chip capacitors 42 are adapted particularly for use in connecting a lead wire or electrode through a hermetically sealed housing to internal electronic components of a medical device while decoupling EMI against entry into the sealed housing. As can be seen from the curve 60 of FIG. 11, staggering of the resonant frequencies provides additional attenuation (filtering effectiveness) at the high frequency end of the spectrum. In other words, the staggering of the resonate dips "fills-in" the high frequency attenuation in order to provide sufficient attenuation throughout the frequency range through which the filter assembly is designed to operate.

FIGS. 12–17 illustrate a number of reduced inductance chip capacitor designs. Any of these improved chip capacitor designs may be mounted directly at the point of lead penetration into, for example, a pacemaker housing by any of the methods described above in connection with FIGS. 1–9. Additional mounting methods or variations will be apparent to those skilled in the art.

Figure 12A:
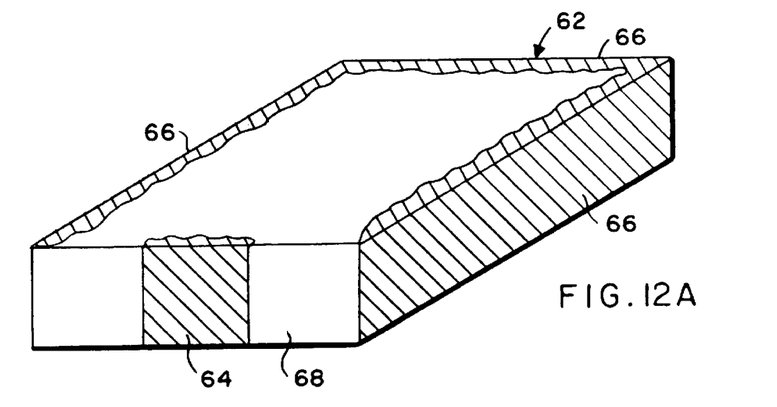
FIG. 12A is a perspective view of the novel chip capacitor.
Figure 12B:
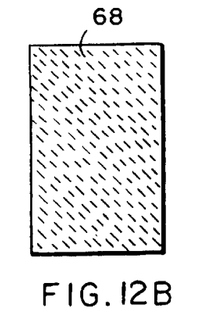
FIG. 12B illustrates a blank, interleaf or cover layer pattern.
Figure 12C:
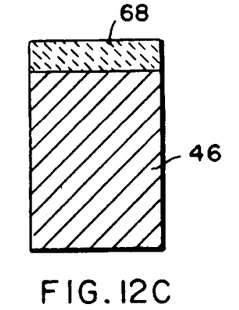
FIG. 12C illustrates a ground electrode plate pattern.
Figure 12D:
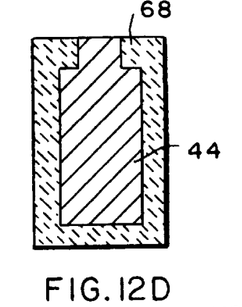
FIG. 12D illustrates an active electrode plate layup pattern.

More particularly, FIGS. 12A–12D illustrate a novel means by which the series inductance of a chip capacitor 62 may be reduced by terminating the second set (or ground) of electrode plates 46 on three sides instead of at only the end. FIG. 12A illustrates a perspective view of the chip capacitor 62 wherein an active metallization band 64 is exposed at one end of the chip capacitor 62, and the ground metallization 66 is exposed on the other three sides of the chip capacitor perpendicular to the planes of the electrode plates 44 and 46. The chip capacitor 62 is otherwise of standard construction, including a ceramic dielectric 68 that has disposed therein alternating layup patterns for the ground electrodes 46 and the active electrodes 44 separated by the ceramic dielectric 68.

Figure 13A:
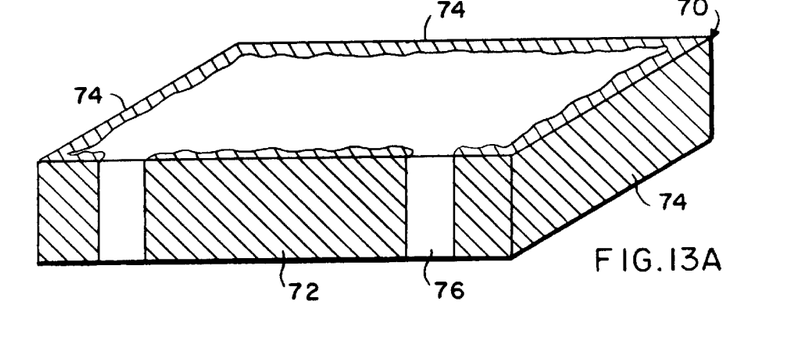
FIG. 13A is a perspective view of the novel chip capacitor.
Figure 13B:
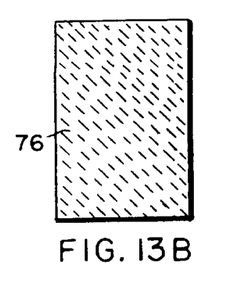
FIG. 13B illustrates a blank, interleaf or cover layer pattern.
Figure 13C:
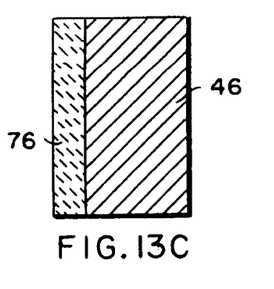
FIG. 13C illustrates a ground electrode plate pattern.
Figure 13D:
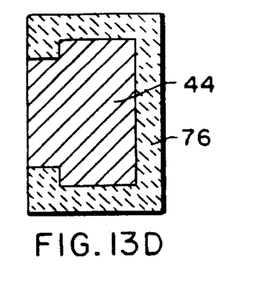
FIG. 13D illustrates an active electrode plate layup pattern.

FIGS. 13A–13D are similar to FIGS. 12A–12D, but show an improved version chip capacitor 70 where the form factor is adjusted to minimize the loop inductance. As was the case above, FIG. 13A illustrates a perspective view of the chip capacitor 70, wherein an active metallization band 72 is exposed at one end of the chip capacitor 70, and the ground metallization 74 is exposed on the other three sides of the chip capacitor perpendicular to the planes of the electrode plates 44 and 46. The chip capacitor 70 is otherwise of standard construction, including a ceramic dielectric 76 that has disposed therein alternating layup patterns for the ground electrodes 46 and the active electrodes 44 separated by the ceramic dielectric 76.

Figure 14A:
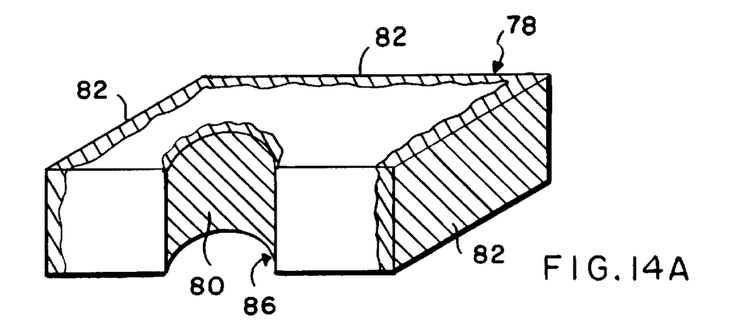
FIG. 14A is a perspective view of the novel chip capacitor.
Figure 14B:
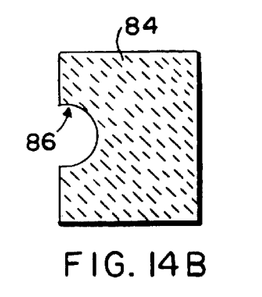
FIG. 14B illustrates a blank, interleaf or cover layer pattern.
Figure 14C:
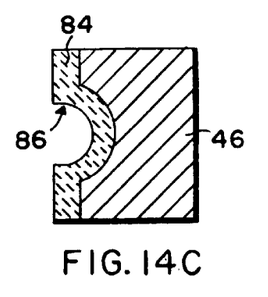
FIG. 14C illustrates a ground electrode plate pattern.
Figure 14D:
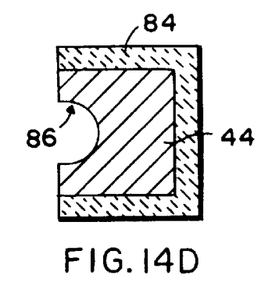
FIG. 14D illustrates an active electrode plate layup pattern.

FIGS. 14A–14D illustrate yet another chip capacitor 78 having qualities similar to the chip capacitors 62 and 70 described above. Namely, FIG. 14A illustrates a perspective view of the chip capacitor 78, wherein an active metallization band 80 is exposed at one end of the chip capacitor 78, and the ground metallization 82 is exposed on the other three sides of the chip capacitor perpendicular to the planes of the electrode plates 44 and 46. The chip capacitor 78 is otherwise of standard construction, including a ceramic dielectric 84 that has disposed therein alternating layup patterns for the ground electrodes 46 and the active electrodes 44 separated by the ceramic dielectric 84. Additionally, the capacitor 78 provides a semicircular recess 86 to facilitate mounting of the chip capacitor 78 directly to a lead at the point of penetration into a device housing.

FIG. 15 illustrates use of two chip capacitors 78' and 78" manufactured as illustrated in FIGS. 14A–14D. The two chip capacitors 78' and 78" are of different size and capacitance value, and are fitted around an exemplary conductive terminal pin 36f. Use of the chip capacitors 78' and 78" having the semicircular recesses 86 reduces the resonant dips of the individual chip capacitors by terminating the ground electrode on three sides. This particular design also reduces the loop inductance because the semi-circular lead recess reduces the loop inductance. Staggering of the resonant dips of the individual capacitors 78' and 78" by using two differently sized capacitors provides improves RF shielding by completely surrounding the terminal pin 36f. Further, by substantially overlying the insulator 40f with the ground electrode plates of the two capacitors 78' and 78", the ground plates, cooperatively with the conductive substrate, form an electromagnetic shield against radiated EMI.

Figure 16A:
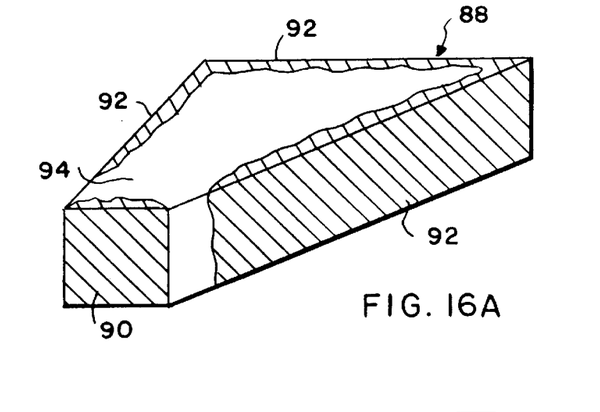
FIG. 16A is a perspective view of the novel chip capacitor.
Figure 16B:
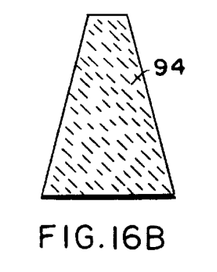
FIG. 16B illustrates a blank, interleaf or cover layer pattern.
Figure 16C:
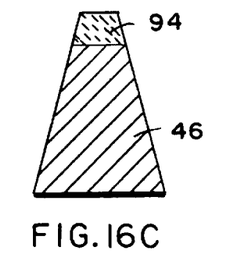
FIG. 16C illustrates a ground electrode plate pattern.
Figure 16D:
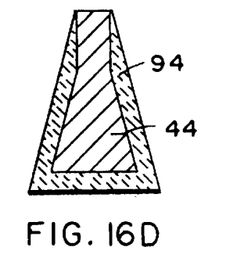
FIG. 16D illustrates an active electrode plate layup pattern.

FIGS. 16A–16D illustrate yet another unique geometry for a chip capacitor 88, wherein the capacitor is wedge-shaped to provide higher volumetric efficiency and shielding when butted around a lead wire. FIG. 16A illustrates a perspective view of the chip capacitor 88, wherein an active metallization band 90 is exposed at one end of the chip capacitor 88, and the ground metallization 92 is exposed on the other three sides of the chip capacitor perpendicular to the planes of the electrode plates 44 and 46. The chip capacitor 88 is otherwise of standard construction, including a ceramic dielectric 94 that has disposed therein alternating layup patterns for the ground electrodes 46 and the active electrodes 44 separated by the ceramic dielectric 94.

FIG. 17 illustrates the manner in which the wedge-shaped chip capacitors 88 may be arranged about a conductive terminal 36g on the face of a conductive ferrule 38g.

From the foregoing it will be appreciated that the electromagnetic interference (EMI) filter assemblies 30 disclosed herein provide for shielding and decoupling of a conductive terminal pin or lead of the type used, for example, in an implantable medical device, against passage of external interference signals, such as caused by digital cellular telephones. The EMI filter assemblies 30a–30g are constructed of relatively inexpensive ceramic chip capacitors 42 which replace the relatively expensive feedthrough filter capacitors described in the prior art. The EMI filter assemblies of the present invention utilize (1) multiple chip capacitors 42 installed directly at the point of lead penetration into the implantable device housing to stagger their self-resonant points in such a way as to provide adequate EMI filter attenuation over a broad filter range, and (2) novel chip capacitor designs which reduce the inductance of the capacitor and/or facilitate packaging at the point of lead penetration into a housing.

Although several embodiments of the invention have been described in detail for purposes of illustration, various modifications may be made without departing from the spirit and scope of the invention.

Accordingly, the invention is not to be limited, except as by the appended claims.

We claim:

1. An electromagnetic interference (EMI) filter assembly disposed at a point of lead penetration through a conductive substrate, comprising:
    at least one conductive terminal associated with the point of lead penetration through the conductive substrate;
    means for mounting the at least one conductive terminal for passage through an opening formed in the conductive substrate with the conductive terminal and the substrate in non-conductive relation; and
    a plurality of chip capacitors of differing capacitance values each having first and second sets of electrode plates, the first set of electrode plates being conductively coupled to the at least one conductive terminal, and the second set of electrode plates being conductively coupled to the conductive substrate.

2. The assembly of claim 1, wherein the at least one conductive terminal comprises a plurality of conductive terminals associated with the point of lead penetration through the conductive substrate, and wherein the assembly includes a plurality of chip capacitors of differing capacitance values associated with each of the plurality of conductive terminals.

3. The assembly of claim 2, including a terminal-to-terminal chip capacitor having a first set of electrode plates coupled to one conductive terminal, and a second set of electrode plates coupled to another conductive terminal.

4. The assembly of claim 2, including asymmetrical groupings of chip capacitors relative to the plurality of conductive terminals.

5. The assembly of claim 1, wherein the conductive substrate comprises metallization applied to an insulative substrate, and wherein the metallization further forms the at least one conductive terminal.

6. The assembly of claim 1, wherein the plurality of chip capacitors incorporate a reduced inductance design wherein the first set of electrode plates terminates on one side of the chip capacitors perpendicular to the first set of electrode plates, and the second set of electrode plates terminates on at least the remaining sides of the plurality of chip capacitors perpendicular to the second set of electrode plates.

7. The assembly of claim 6, wherein the one side of the chip capacitors whereat the first set of electrode plates terminate includes a semicircular recess, and wherein the at least one conductive terminal includes a terminal pin received within the semicircular recess.

8. The assembly of claim 6, wherein the chip capacitors comprise a wedge-shaped chip capacitor having the second set of electrode plates terminating on three sides thereof.

9. An electromagnetic interference (EMI) filter assembly, comprising:

at least one conductive terminal;

means for mounting the at least one conductive terminal within an opening formed in a conductive substrate, with the conductive terminal and the substrate in non-conductive relation;

a first chip capacitor having first and second sets of electrode plates, wherein the first set of electrode plates is conductively coupled to the at least one conductive terminal, and the second set of electrode plates is conductively coupled to the conductive substrate; and a second chip capacitor having a capacitance value different from that of the first capacitor, the second chip capacitor having first and second sets of electrode plates, wherein the first set of electrode plates is conductively coupled to the at least one conductive terminal, and the second set of electrode plates is conductively coupled to the conductive substrate.

10. The assembly of claim 9, wherein the at least one conductive terminal comprises a plurality of conductive terminals, and wherein a plurality of chip capacitors are associated with each of the plurality of conductive terminals.

11. The assembly of claim 10, including a terminal-to-terminal chip capacitor having one set of electrode plates coupled to one conductive terminal, and another set of electrode plates coupled to another conductive terminal.

12. The assembly of claim 10, including asymmetrical groupings of chip capacitors relative to the plurality of conductive terminals.

13. The assembly of claim 9, wherein the conductive substrate comprises a ferrule conductively attachable to a housing for an electronic device.

14. The assembly of claim 9, wherein the at least one conductive terminal and the conductive substrate have matched coefficients of expansion.

15. The assembly of claim 14, wherein the conductive substrate comprises metallization applied to an insulative substrate.

16. The assembly of claim 15, wherein the metallization applied to the insulative substrate further forms the at least one conductive terminal.

17. The assembly of claim 9, wherein the at least one of the first or second chip capacitors comprises a reduced inductance design wherein the first set of electrode plates terminates on one side of the chip capacitor perpendicular to the first set of electrode plates, and the second set of electrode plates terminates on at least the remaining sides of the chip capacitor perpendicular to the second set of electrode plates.

18. The assembly of claim 17, wherein the one side of the chip capacitor, whereat the first set of electrode plates terminate includes a semicircular recess.

19. The assembly of claim 18, wherein the at least one conductive terminal includes a terminal, pin received within the semicircular recess.

20. The assembly of claim 17, wherein the at least one chip capacitor comprises a wedge-shaped chip capacitor having the second set of electrode plates terminating on three sides thereof.

* * * * *